US 7,567,734 B2

United States Patent
Dai et al.

(10) Patent No.: US 7,567,734 B2
(45) Date of Patent: Jul. 28, 2009

(54) RIDGE WAVEGUIDE OPTICAL SENSOR INCORPORATING A BRAGG GRATING

(75) Inventors: Xiaoli Dai, Ottawa (CA); Stephen J. Mihailov, Kanata (CA); Robert B. Walker, Spencerville (CA); Chantal Blanchetiere, Ottawa (CA); Claire Callender, Nepean (CA); Huimin Ding, Nepean (CA); Ping Lu, Ottawa (CA); Dan Grobnic, Ottawa (CA); Christopher W. Smelser, Ottawa (CA); Gino Cuglietta, Kanata (CA)

(73) Assignee: Her Majesty the Queen in right of Canada, as represented by the Minister of Industry, through the Communications Research Centre Canada, Ottawa, Ontario (CA)

( * ) Notice: Subject to any disclaimer, the term of this patent is extended or adjusted under 35 U.S.C. 154(b) by 0 days.

(21) Appl. No.: 12/222,392

(22) Filed: Aug. 8, 2008

(65) Prior Publication Data
US 2009/0041405 A1   Feb. 12, 2009

Related U.S. Application Data

(60) Provisional application No. 60/954,854, filed on Aug. 9, 2007.

(51) Int. Cl.
*G02B 6/00* (2006.01)
*G02B 6/26* (2006.01)
(52) U.S. Cl. .............................. 385/12; 385/10; 385/30; 385/32
(58) Field of Classification Search .................. None
See application file for complete search history.

(56) References Cited

U.S. PATENT DOCUMENTS

| 4,518,219 | A   | 5/1985 | Leonburger et al. |
| 6,915,028 | B2* | 7/2005 | Lyons .......................... 385/12 |
| 6,993,221 | B2  | 1/2006 | Mihailov et al. |
| 7,184,135 | B2  | 2/2007 | Lafont et al. |
| 7,391,936 | B2* | 6/2008 | Pau et al. ....................... 385/12 |

(Continued)

OTHER PUBLICATIONS

Schroeder et al, "Meis. Sci. Technol." 12, pp. 757-764 (2001).

(Continued)

*Primary Examiner*—Tina M Wong
(74) *Attorney, Agent, or Firm*—Teitelbaum & MacLean; Neil Teitelbaum; Doug MacLean (57) ABSTRACT

An optical sensor for sensing information relating to an analyte liquid or gas, has a a planar substrate having a refractive index $n_c$. The planar substrate supports a ridge waveguide having an unclad top portion having a refractive index $n_r$. The substrate serves as cladding layer for the ridge waveguide at a location where the ridge waveguide contacts the substrate. A Bragg grating inscribed in the ridge waveguide has two modes for providing information relating to both temperature and refractive index of the surrounding analyte liquid or gas. A cladding mode has a different response to the analyte when compared to a Bragg resonance response. Both modes have a same reaction to temperature, wherein said Bragg grating is formed within the unclad region of ridge waveguide, wherein $n_c < n_r$. Advantageously multiple parameters can be sensed using only a single Bragg grating.

23 Claims, 10 Drawing Sheets
(1 of 10 Drawing Sheet(s) Filed in Color)

U.S. PATENT DOCUMENTS 7,486,855 B2 * 2/2009 Smith et al. .................. 385/32

OTHER PUBLICATIONS

Pereira et al, "Opt. Eng." 43, pp. 299-304 (2004).
Chryssis et al, "IEEE Quan. Electron." 11, pp. 864-872 (2005).
Shu et al, "Opt. Lett." 26, pp. 774-776 (2001).
Kang e tal, "IEEE Photon." Tech. Lett. 10, pp. 1461-1463 (1998).
Chan et al, "Appl. Opt."46, pp. 1142-1149 (2007).
Asseh et al, "Fib. Int. Opt." 17, pp. 51-62 (1998).
Veldhuis et al, "Pure Appl. Opt." 7, L23-L26 (1998).
Sparrow et al, "17$^{th}$ International Conf. on Optical Fibre Sensors, Proc. of SPIE," vol. 5855, pp. 888-891 (2005).
Emmerson et al, "Appl. Opt." 44, pp. 5042-5045(2005).
Dai et al, "Meas. Sci. Technol." 17, pp. 1752-1756 (2006).

* cited by examiner

RIDGE WAVEGUIDE OPTICAL SENSOR INCORPORATING A BRAGG GRATING

CROSS-REFERENCE TO RELATED APPLICATIONS

The present invention claims priority from U.S. Provisional Patent Application No. 60/954,854 filed Aug. 9, 2007, which is incorporated herein by reference.

FIELD OF THE INVENTION

The present invention relates to a sensing apparatus and method for measurement of refractive index of a surrounding liquid or gas, and more particularly to a Bragg grating sensor inscribed in a ridge waveguide. The sensing apparatus is substantially insensitive to fluctuations in temperature.

BACKGROUND OF THE INVENTION

With their miniature size, non-invasive and rapid detection, a waveguide Bragg grating refractometric sensor can be a useful tool for chemical analysis and biomedical testing, where the evanescent field of the fundamental mode propagating in a waveguide containing a Bragg grating can interact with liquids and gases surrounding the waveguide in order to measure small changes in the refractive index of the surrounding liquid. Measurements from Bragg grating based refractometers however often can be distorted by fluctuations in the ambient temperature. For temperature insensitive sensors based on fiber Bragg gratings, several techniques have been proposed to discriminate between Bragg resonance spectral shifts associated with refractive index measurements and those induced by fluctuations in temperature. These techniques are implemented by using: a second Bragg grating in a side-polished fiber Bragg grating refractometer as taught by Schroeder et al. in *Meas. Sci. Technol.* 12, p. 757-764, 2001 and Pereira et al. in *Opt. Eng.* 43, p. 299-304, 2004 incorporated herein by reference; higher order modes in an etched-core of a fiber Bragg grating sensor as taught by Chryssis et al. in *IEEE Quan. Electron.* 11, pp 864-872, 2005 incorporated herein by reference; a single sampled fiber Bragg grating possessing the responses of the core guided Bragg grating and cladding guided long period grating as taught by Shu et al. in Opt. Lett. 26, 774-776, 2001 incorporated herein by reference, and; cladding modes in a tilted fiber Bragg grating sensor as taught by Kang, et al. in *IEEE Photon. Tech. Lett.* 10, pp. 1461-3, 1998; Chan et al. *Appl. Opt* 46 pp. 1142-1149, 2007, and Laffont et al. in U.S. Pat. No. 7,184,135, also incorporated herein by reference. To increase the interaction of the surrounding medium with the evanescent field about the waveguide core, the fiber cladding is often removed at the location of the Bragg grating. Etched fibers either as a side polish or symmetric tapered etch about the core are taught by Asseh et al. in *Fib. Int. Opt.* 17 pp. 51-62, 1998, incorporated herein by reference.

These prior art gratings are instructive and provide a useful function, however they are known to suffer from some limitations in terms of the spatial accuracy of the temperature measurement and the mechanical strength of the device. For the case of dual gratings as taught by Schroeder et al., the temperature monitoring grating and the index monitoring grating are at different locations within the fluid being measured. However, it is more accurate to have both measurements performed at the same location. The requirement to improve the sensitivity of the fiber grating refractometers by polishing and etching as taught by Asseh et al. leads to devices that are mechanically weak and fragile. The use of tilted fiber gratings improves the mechanical strength of the grating refractometer and simultaneous monitoring of the induced core and cladding mode resonances can be used to monitor both temperature and index changes at the identical location within the fluid. Because of the flexible nature of optical fibers however, the tilted grating refractometers suffer from the limitation that the cladding mode resonances, which are used to monitor the temperature, are sensitive to physical changes across the fiber cross-section such as shear strains arising from fiber bending.

Another technique for simultaneous measurement of temperature and refractive index with a fiber grating is by the use of a single sampled fiber Bragg grating as taught by Shu et al. in Opt. Lett. 26, 774-776, 2001, incorporated herein by reference. The sampled fiber grating possesses properties that result in both core guided Bragg grating reflectivity responses and cladding guided long period grating responses. The long period grating response is much more sensitive to external refractive index changes than the core Bragg grating response while the core grating response is much more sensitive to temperature. Aside from the limitations resulting from fiber flexibility as stated for the tilted grating refractometer, the sampled fiber Bragg grating refractometer has the additional limitation that the spectral response of the cladding guided long period grating resonance is spectrally broad (>10 nm) making high accuracy measurements of small wavelength shifts difficult. The difference in temperature sensitivities between the core guided Bragg grating and the cladding guided long period grating also need to be taken into account.

The inherently robust nature of integrated optical devices such as planar waveguides make them better suited for refractometer devices than optical fiber from a mechanical stability perspective. In addition other functionalities can be incorporated into planar waveguide. Incorporation of corrugated Bragg gratings that are etched into the core of buried waveguides once the cladding is removed by chemical etching can be achieved as shown by Veldhuis et al. in Pure Appl. Opt. 7, L23-L26 (1998) incorporated herein by reference. Direct UV laser inscribed waveguides and superimposed UV induced gratings were used to fabricate a refractometric device by etching away the top cladding layer on a buried UV-induced waveguide at the location where a grating was UV laser induced as demonstrated by Sparrow et al. in 17th International Conference on Optical Fibre Sensors, Proc. of SPIE Vol. 5855, p. 888-891 (2005) and Emmerson et al. in Appl. Opt. 44, 5042-5045, (2005) incorporated herein by reference.

These prior art planar waveguide gratings provide a useful function, however they are known to suffer from some limitations. In order to measure the refractive index of a fluid, removal of a portion of the surface cladding layer by chemical etching is required in order to access the waveguide core. In the case of Veldhuis et al. an etch process is also required for the Bragg grating fabrication which is an exacting labour intensive process. In *Meas. Sci. Technol.* 17, pp. 1752-1756, 2006, Dai et al. teach a technique for manufacturing a highly sensitive waveguide Bragg grating (WBG) sensor for measuring small changes in the refractive index of a surrounding liquid was developed. By using a ridge waveguide with a small core that is absent a top cladding layer, the evanescent field interaction of the guided mode with the liquid analyte was enhanced. The ridge waveguide is more easily fabricated than the planar waveguide structure as the processing step of adding a top cladding layer is removed. The average sensitivity measured via a shift in the resonance wavelength of the Bragg grating was as high as 1 pm of wavelength shift for a change of 4×10⁻⁵ in the refractive index on the liquid layer over top the ridge waveguide core. However, the device was sensitive to temperature change as the Bragg wavelength shifted with temperature (~11 pm/° C. in silica waveguides). It was also found that the refractometer could be made more sensitive by having narrower ridge waveguide structures.

It is an object of this invention to overcome the aforementioned limitations of the prior art fiber Bragg grating based refractometers, mainly reduction in mechanical reliability to achieve improved sensitivity and thermal stability. In this invention a technique for creating a substantially temperature insensitive refractometer that utilizes core and cladding modes and/or polarization dependent TE and TM waveguide modes in an open-top ridge waveguide architecture absent a cladding layer in order to discriminate between changes in temperature and refractive index is disclosed.

SUMMARY OF THE INVENTION

In accordance with an embodiment of the invention there is provided, an optical sensor for sensing information relating to an analyte liquid or gas, comprising:

a planar substrate having a refractive index $n_c$;

a ridge waveguide having at least a region thereof unclad and having a refractive index $n_r$ wherein said ridge waveguide is formed upon and supported by substrate, and wherein the substrate serves as cladding layer for the ridge waveguide at a location where the ridge waveguide contacts the substrate; and, a Bragg grating having two modes for providing information relating to both temperature and refractive index of the surrounding analyte liquid or gas, wherein a cladding mode has a different response to the analyte when compared to a Bragg resonance response, while both modes have a same reaction to temperature, wherein said Bragg grating is formed within the unclad region of ridge waveguide, wherein $n_c<n_r$. A first resonance mode may be a cladding mode and a second resonance mode may be a retroreflective Bragg resonance. Alternatively the first resonance mode may be the TE polarization mode of the Bragg resonance and the second resonance mode may be the TM polarization mode of the Bragg resonance.

In a preferred embodiment of the invention, the ridge waveguide has a square or rectangular cross-section at least three sides of the ridge waveguide are unclad in the unclad region. In this instance the substrate provides a structural cladding to the unclad ridge waveguide and the surrounding environment provides a functional cladding to the unclad ridge waveguide.

In accordance with an aspect of the invention an apparatus for measuring the refractive index of an analyte test liquid or gas is provided comprising a chip having a ridge waveguide absent a top cladding layer having a Bragg grating formed therein at a selected location in said waveguide for reflecting light with a selected plurality of contiguous wavelengths provided by a source of light having emission within said selected plurality of bandwidths, said source being optically coupled to said waveguide at an end thereof for transmitting said light into said waveguide; and wherein the apparatus includes a means for controlling the state of polarization of said light; an optical fiber coupled to the output of said waveguide for directing light transmitted from said grating to a location external of said waveguide; a detector for receiving said transmitted light from said grating, wherein the detector analyzes the change in the spectral response of said transmitted light from said grating.

In an alternative embodiment the sensor could be used to measure pressure of the analyte fluid; wherein the pressure would translate into mechanical deformation of the ridge waveguide, which could then be discriminated from temperature and refractive index.

An important aspect of this invention is that it allows plural parameters such as both temperature and refractive index of an analyte to be determined using a single Bragg grating using cladding modes and Bragg resonance modes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is now described with reference to the drawings in which:

FIG. 1b is an isometric view of the open-top waveguide shown in FIG. 1a.

DETAILED DESCRIPTION OF THE INVENTION

Figure 1A:
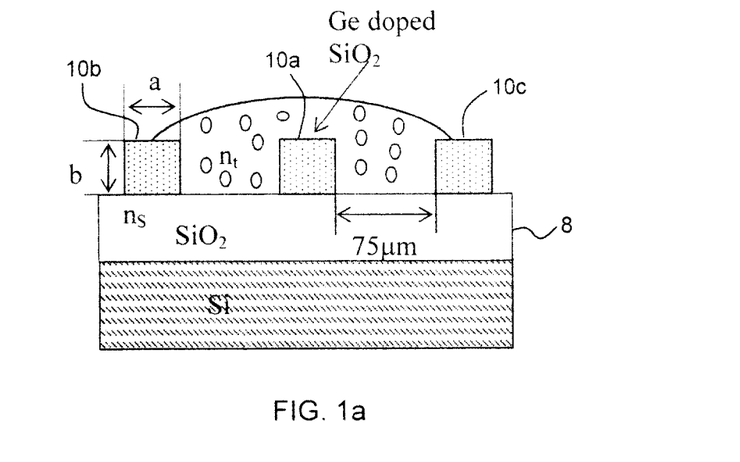
FIG. 1a is a cross sectional view of an open-top ridge waveguide without top cladding.
Figure 1B:
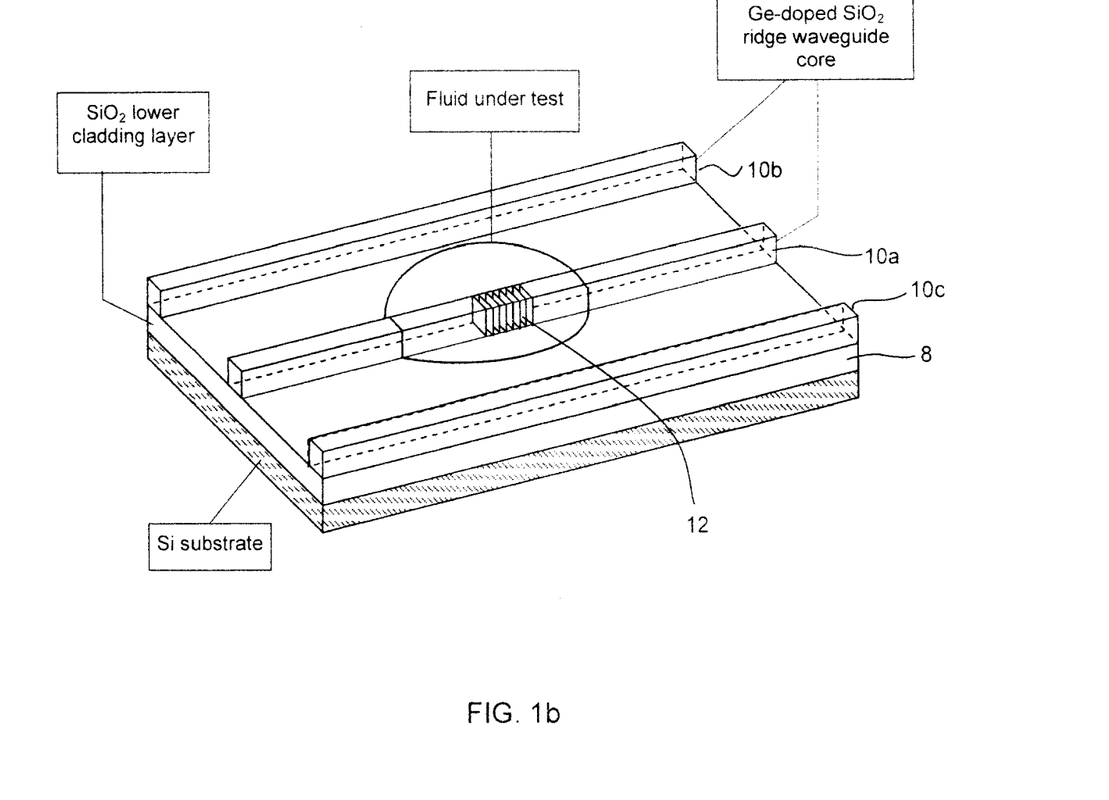

Referring now to FIG. 1a an open-top rib or ridge waveguide is as shown. FIG. 1b shows a cross section of the structure shown in FIG. 1a. More particularly a center ridge waveguide 10a absent a top cladding layer contains a photo-induced Bragg grating 12 supported by a cladding layer 8 which is tested as a refractometer by coupling a light source into the end of the waveguide. Two adjacent waveguides 10b and 10c also supported by the cladding layer 8 are optionally provided to act as a barrier and to partially prevent the liquid from flowing away from the waveguide 10a containing the grating. The adjacent waveguides 10b and 10c do not contribute to the device performance. The guided light provided to the center waveguide 10a couples evanescently into the surrounding liquid through the top and sides of the waveguide. The three waveguides shown in FIGS. 1a and 1b have the same width versus height dimension a×b and are separated by 75 μm. Three different sets of waveguide dimensions were used in the experiments: 7.7 μm×5.6 μm, 6.6 μm×5.6 μm, and 5.7 μm×5.6 μm. As an open-top ridge waveguide 10a exposes three sides of the core (~270°) to a surrounding liquid, the core modes associated with these structures exhibit higher sensitivity to the index of the analyte liquid than is present in side-etched waveguide designs. When a Bragg grating 12 is induced in the core of an open-top ridge waveguide 10a, core and cladding resonances are observed when the light modes guided by the core and under-cladding 8 are phase-matched by the grating structure. Both the core and cladding resonances are sensitive to the liquid refractive index on the top layer of the open-top ridge waveguide 10a. However, because modes of the under-cladding 8 have a different degree of exposure and are somewhat shielded by the ridge waveguide 10a itself, the sensitivity of the cladding modes to the refractive index of the analyte liquid is different from the sensitivity of the core mode. The core and cladding mode sensitivities to temperature fluctuations however, are more closely matched as the thermo-optic coefficients of the germanium doped silica waveguide core and cladding materials are similar to each other. When a Bragg grating 12 is induced in the core of an open-top ridge waveguide with a large birefringence, TE and TM resonances are observed when the light guided by the core is phase matched by the grating structure. The TE and TM resonances have different sensitivities to the liquid refractive index on the top layer of the open-top ridge waveguide. The TE and TM sensitivities to temperature fluctuations however, are more closely matched. These characteristics can be used to decouple fluctuations of the Bragg resonance of one mode due to temperature from those changes that are due to variation in the refractive index of the analyte liquid.

Figure 2:
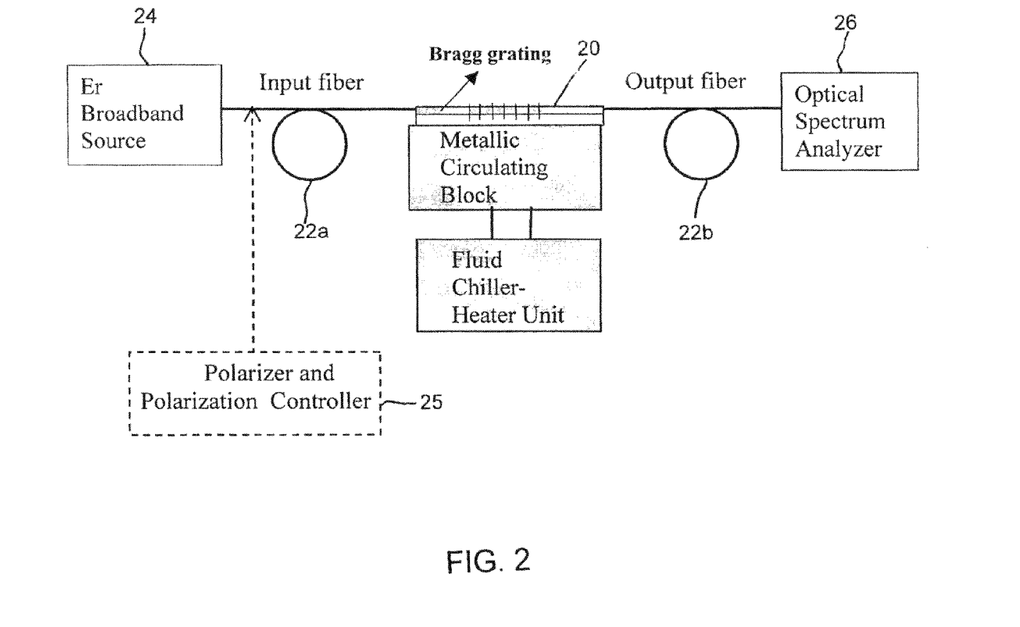
FIG. 2 is the configuration of measurement setup

As shown in FIG. 1, ridge waveguides 10a, 10b and 10c were fabricated in a 6±0.5 μm thick Ge-doped SiO$_2$ layer grown by flame hydrolysis deposition (FHD) on a 7 μm layer of thermal silicon dioxide on silicon. The ridges were produced using standard photolithography and reactive ion etching (RIE) using a CHF$_3$/O$_2$ gas mixture. The core layer index, n$_g$ was measured before etching by prism coupling at 1537 nm to be 1.4545±0.0004. The bottom cladding index n$_s$ was 1.4436, which was 0.75±0.07% less than n$_g$. The dimensions of the waveguides, as measured using scanning electron microscopy were 7.7 μm×5.6 μm, 6.6 μm×5.6 μm, and 5.7 μm×5.6 μm respectively. The distance between two adjacent ridges was 75 μm. On a wafer patterned with different core size ridge waveguides, Bragg gratings were written using a single zero-order nulled phase mask and an ArF excimer laser with an emission wavelength of 193 nm. With a UV cylindrical lens, the laser beam was focused to a spot size of 5 mm×300 μm onto the wafer surface. A strong Bragg grating 12 with index modulation Δn~9×10$^{-4}$ was induced in the hydrogen loaded 6.6 μm×5.6 μm waveguide with 40 Hz, 100 mJ/cm$^2$/pulse of unpolarized UV excimer irradiation. The laser beam was polarized to reduce the birefringence of the device. The total UV exposure for the fabrication of the Bragg grating with −21 dB transmission and 0.7 nm bandwidth is 1 kJ/cm$^2$. The section of the waveguide that contains the Bragg grating with the 5 mm length is covered with the analyte liquid entirely when the refractive index changes of the liquid were measured. The experimental setup is shown in FIG. 2 where the waveguide chip 20 shown in FIG. 1a is optically coupled to an input single mode optical fiber 22a and an output single mode optical fiber 22b. A light source 24 provides broadband light to the probe waveguide chip 20. To monitor the changes of core and cladding modes with the refractive index of the liquid analyte and temperature, the broadband light from a 980 nm-pumped erbium-doped fiber was coupled via the single mode fiber 22a into the core of the open-top waveguide. The transmitted light was out-coupled to the single mode fiber 22b and monitored by using an optical spectrum analyzer 26. To monitor the polarization spectral response of the grating, a polarization controller 25 is placed in line with the optical source 24 and is coupled into the planar waveguide 22a. Bragg wavelengths for TE and TM polarizations were distinguished using a half wave plate. It should be noted that in some instances it is preferred to write the Bragg grating by having the polarization of the laser only along the waveguide axis so as to enhance the difference in TE and TM modes so that unique polarization dependent information can be gleaned from the TE mode and from the TM mode response.

Figure 3:
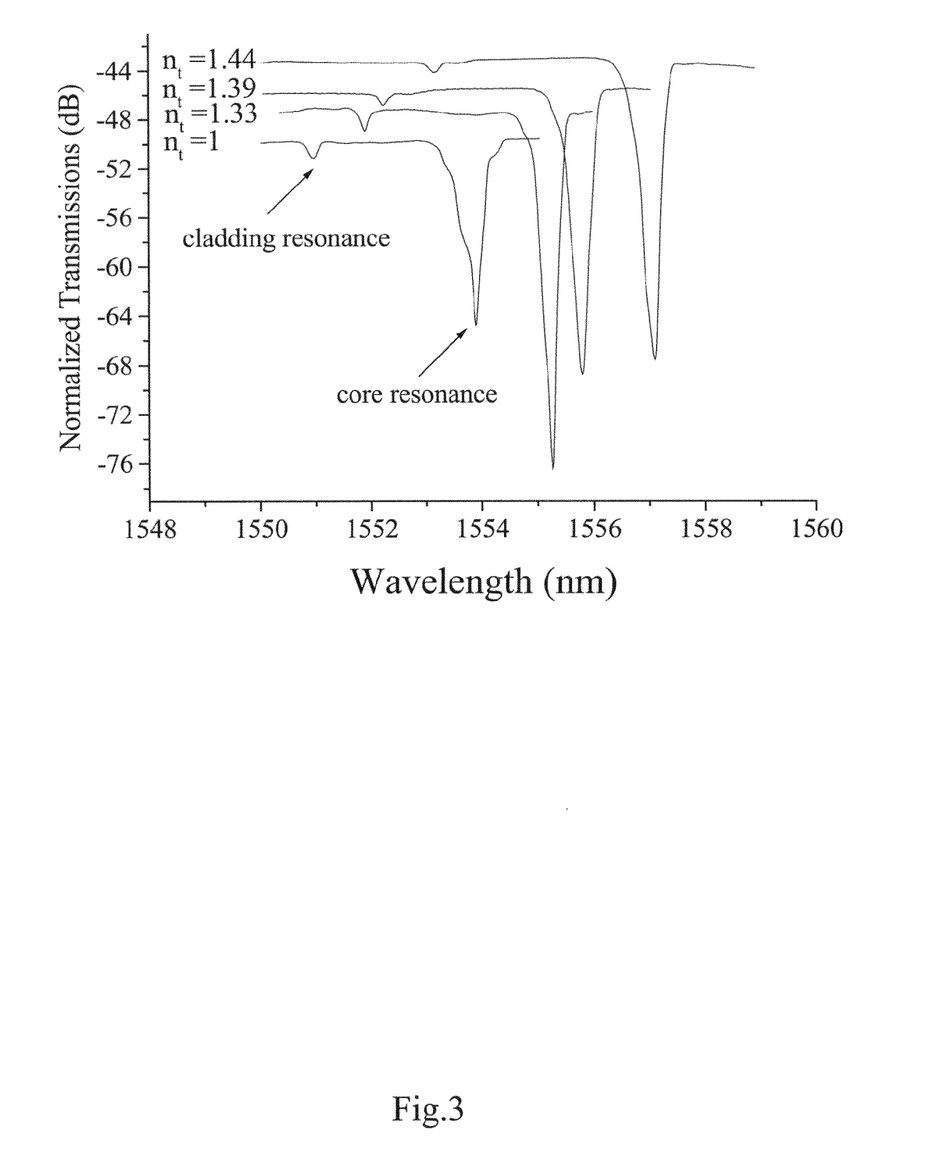
FIG. 3 is the spectra of core and cladding Bragg resonance shifts with the change of the refractive index of the analyte liquid.
Figure 4:
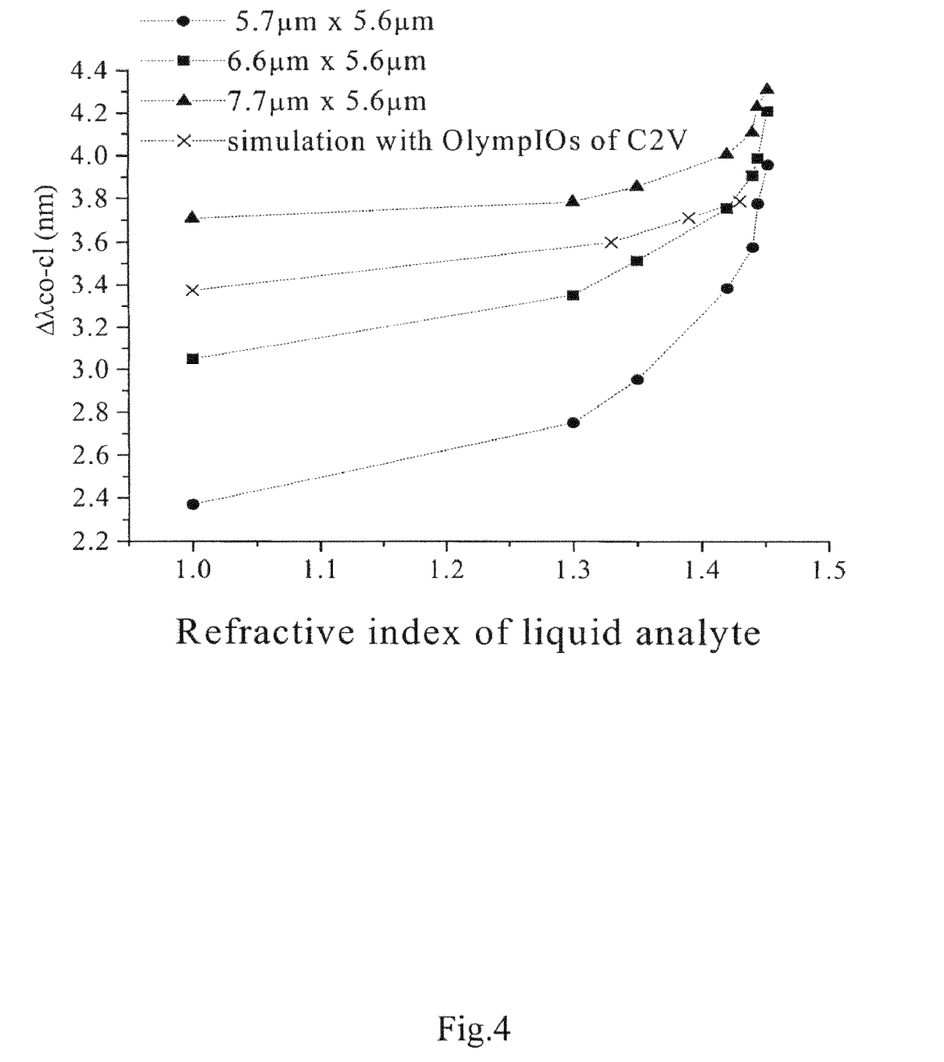
FIG. 4 is the difference of cladding and core resonances as a function of the test liquid refractive index for the devices with waveguide cores were 7.7 μm×5.6 μm, 6.6 μm×5.6 μm, and 5.7 μm×5.6 μm denoted by triangles, squares and circles respectively. Simulated responses for a 6.6 μm×5.6 μm are denoted by crosses.
Figure 5:
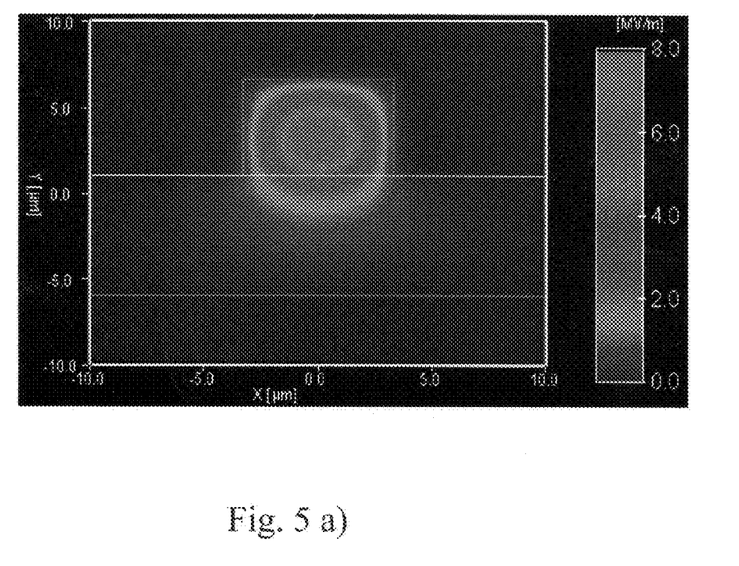
FIGS. 5a and 5b denote the simulation results of the field distributions of core mode and cladding mode in TE polarization: (a) core mode; (b) cladding mode

First, the characterization of the device as a refractometer by considering the variation of core and cladding modes was carried out. Cargille liquids were used to test the devices at 22° C. Liquids with different refractive indices n$_t$ were dropped onto the top surface of the waveguide. The transmission spectra of the device having waveguide core size of 6.6 μm×5.6 μm is shown in FIG. 3. For gratings that were written with their planes orthogonal to the waveguide axis, as presented here, much stronger coupling to the core mode as opposed to the cladding mode was observed. From the point of view of utilizing both core and cladding modes resonances to decouple temperature and index change information, it is desirable to increase the strength of the cladding mode resonance making it more easily detectable. This can be easily achieved by blazing or tilting the grating slightly with respect to the optical axis of the waveguide. Both core and cladding mode resonances were sensitive to changes of the analyte index n$_t$. From 1 to 1.44 the core mode wavelength shifted more than the cladding mode wavelength resulting in a core-cladding mode wavelength difference $\Delta\lambda_{co-cl}$. Unlike similar devices in optical fiber, the Bragg resonance of the core mode was more sensitive than the cladding mode resonance to the refractive index change of the liquid on top of the waveguide. Devices with waveguide core sizes of 7.7 μm×5.6 μm, and 5.7 μm×5.6 μm were also tested. The results were plotted and are show in FIG. 4. It is shown that the sensitivity to the analyte increased with decreasing waveguide core width. As the sensitivity S$_e$ is defined as $\Delta(\lambda_{core}-\lambda_{cladding})/\Delta n$, it is dominated by the change of the core mode evanescent sensitivity that increases with decreasing core width. The sensitivity measured via the variation of $\Delta\lambda_{co-cl}$ with n$_t$ corresponded to a 1 pm increase of $\Delta\lambda_{co-cl}$. The small core size 5.7 μm× 5.6 μm device had the highest sensitivity. The sensitivity increased slowly for low analyte indices, but increased more rapidly as n$_t$ approached that of the waveguide core n$_g$. From the curve in FIG. 4 for the 5.7×5.6 μm waveguide, the sensitivity of n$_t$ from 1.436 to 1.4544 is 2.7×10$^{-5}$ of n, change for 1 pm variation of $\Delta\lambda_{co-cl}$, the sensitivity of n$_t$ from 1.436 to 1.418 is 8×10$^{-5}$ of n, change for 1 pm variation of $\Delta\lambda_{co-cl}$, the sensitivity of n$_t$ from 1.35 to 1.42 is 1.67×10$^{-4}$ of n$_t$ change for 1 pm variation of $\Delta\lambda_{co-cl}$, the sensitivity of n$_t$ from 1.3 to 1.35 is 2.38×10$^{-4}$ of n$_t$ change for 1 pm variation of $\Delta\lambda_{co-cl}$, and the sensitivity of n$_t$ from 1 to 1.3 is 7.6×10$^{-4}$ of n$_t$ change for 1 pm variation of $\Delta\lambda_{co-cl}$. As a comparison, the field distributions of the core and cladding modes of the waveguide having core dimensions of 6.6 μm×5.6 μm, were simulated by a generic finite difference method using the commercial software package OlympIOs of C2V. The resultant field distributions of the core and cladding modes for the device are shown in FIG. 5. It is clear that the cladding mode is less sensitive to the external index changes than core mode, because the cladding mode field is less confined in core layer than in cladding layer. The corresponding $\Delta\lambda_{co-cl}$ as a function of external index resulting from the simulation was also plotted in FIG. 4.

Figure 6:
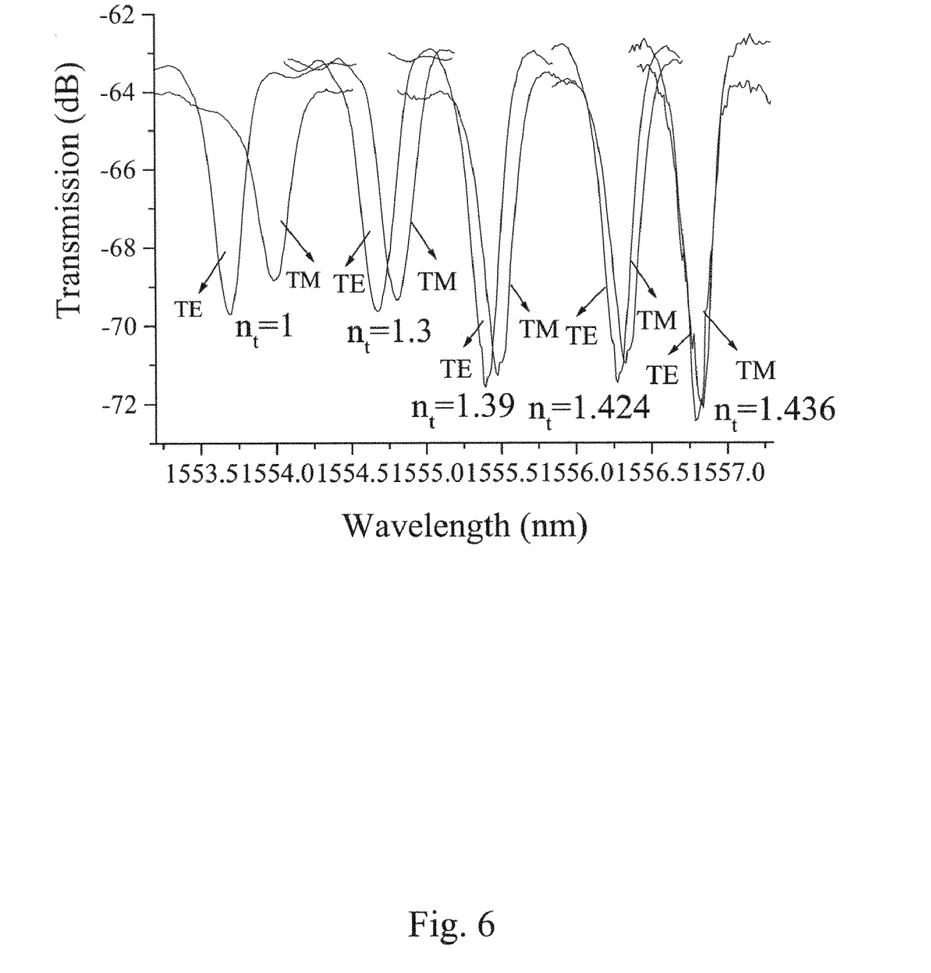
FIG. 6 presents the spectra of TE and TM Bragg resonance shifts with the change of the refractive index of the analyte liquid.
Figure 7:
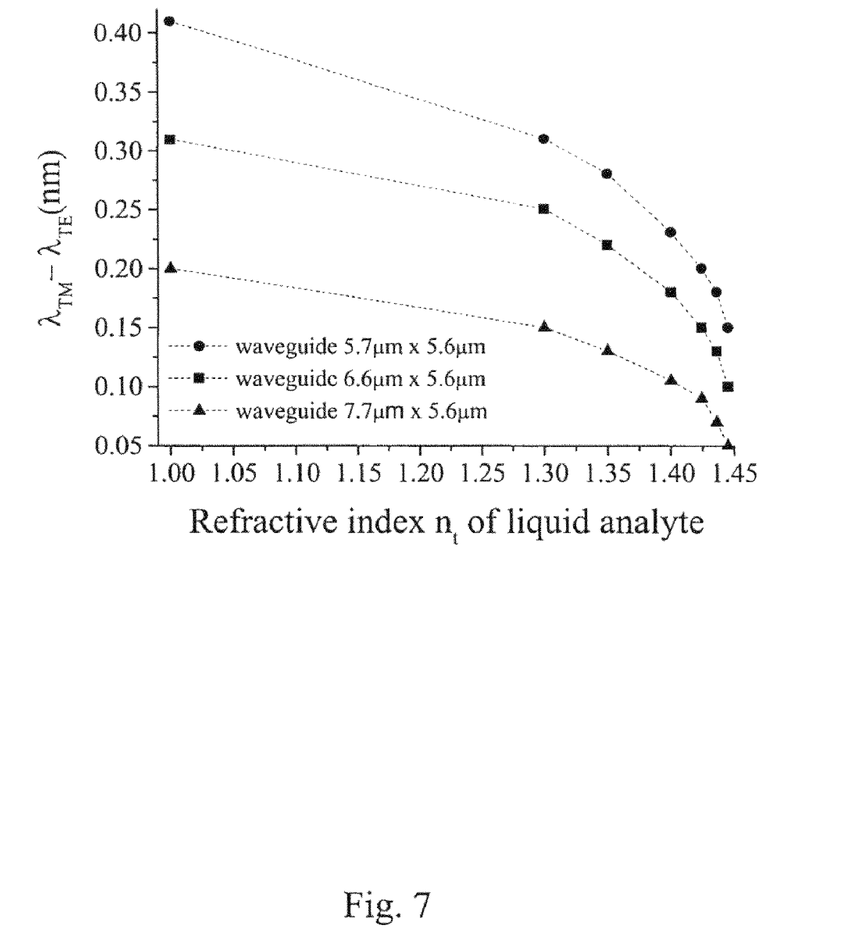
FIG. 7 presents the difference of TE and TM resonances as a function of the test liquid refractive index for the devices with waveguide cores were 7.7 μm×5.6 μm, 6.6 μm×5.6 μm, and 5.7 μm×5.6 μm denoted by triangles, squares and circles respectively.

Secondly, the characterization of the device as a refractometer by considering TE and TM modes was carried out. Cargille liquids were used to test the devices at 22° C. Liquids with different refractive index $n_t$ from 1 to 1.436 were dropped onto the top surface of the waveguide whose core size is 6.6 μm×5.6 μm. The Bragg wavelengths shifted with the change of the analyte index. The transmission spectra are shown in FIG. 6. Results indicated that the devices were polarization dependent. Both TE and TM Bragg resonances were sensitive to the changes of the analyte index $n_t$. The devices with waveguide core sizes of 7.7 μm×5.6 μm, and 5.7 μm×5.6 μm were also tested. The wavelength difference $\Delta\lambda_{TM-TE}$ varied with the analyte index $n_t$ is plotted in FIG. 7. It is clear that the sensitivity defined as the variation of $\Delta\lambda_{TM-TE}$ with $\Delta n_t$ increased with decreasing waveguide core width. The small core size 5.7 μm×5.6 μm device had the highest sensitivity. The sensitivity increased slowly for low analyte indices, but increased more rapidly as $n_t$ approached that of the waveguide core $n_g$. From the curve in FIG. 7 for the 5.7×5.6 μm waveguide, the sensitivity of $n_t$ from 1.425 to 1.4544 is 3×10$^{-4}$ of $n_t$ change for 1 pm variation of $\Delta\lambda_{TM-TE}$, the sensitivity of $n_t$ from 1.3 to 1.42 is 5×10$^{-4}$ of $n_t$ change for 1 pm variation of $\Delta\lambda_{TM-TE}$, the sensitivity of $n_t$ from 1 to 1.3 is 3×10$^{-3}$ of $n_t$ change for 1 pm variation of $\Delta\lambda_{TM-TE}$. The waveguide gratings characterized here were inscribed using the technique as disclosed in Dai et al. *Opt. Comm.*, vol. 248, no. 1-3, pp. 123-130, 2005, incorporated herein by reference, where a polarized UV inscription laser was used to minimize the waveguide birefringence by orienting the polarization of the inscription UV laser normal to the waveguide axis. By reorienting the polarization direction of the UV beam so that it is along the ridge waveguide axis, waveguide birefringence would be significantly enhanced thus enhancing the $\Delta\lambda_{TM-TE}$ with $\Delta n_t$, and the sensitivity of the refractometer when considering TE and TM mode propagation.

Figure 8:
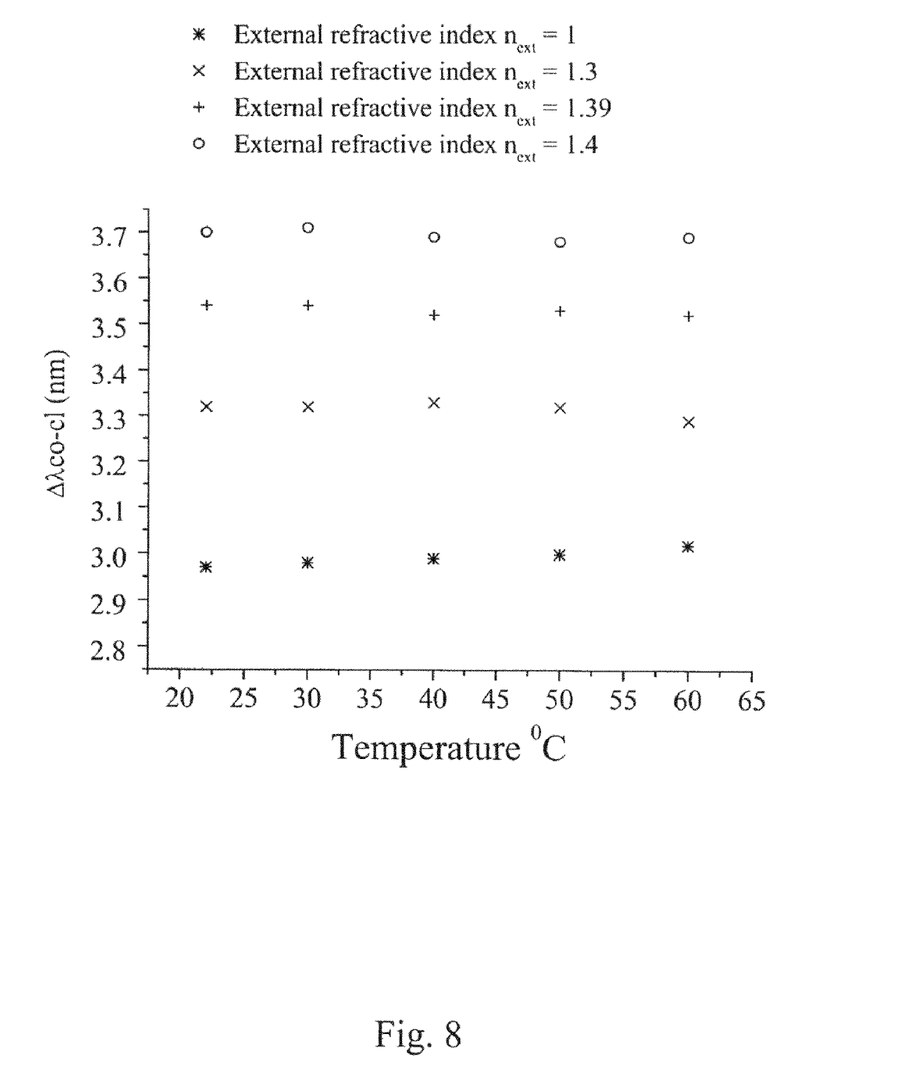
FIG. 8 presents the test results of the difference of cladding and core mode resonances varying with temperature respectively for the device whose waveguide core is of 6.6 μm× 5.6 μm with air top layer.

The temperature stability of the device was determined by considering the variation of core and cladding modes. The waveguide was mounted on a metallic block in which liquid at a constant temperature could be circulated. The temperature of the device was varied in a stepwise fashion through a fluid chiller-heater unit 29a connected to the metallic circulating block 29b and the temperature was measured at the surface of the block. The variation of $\Delta\lambda_{co-cl}$ with temperature (22° C. to 65° C.) was measured for a device with a waveguide core size of 6.6 μm×5.6 μm using index-matching fluids with refractive indexes of 1 (air), 1.3, 1.33, and 1.4, respectively. The results were shown in FIG. 8. The variation of $\Delta\lambda_{co-cl}$ with temperature was ~0.5 pm/° C. The temperature dependence of the cladding mode Bragg resonance was similar to that of the core mode Bragg resonance. With the exception of $n_t$=1, the variation of $\Delta\lambda_{co-cl}$ decreased with increasing temperature because of the thermal dependence of the refractive index of the matching oils. For the liquids whose refractive indices are 1.33, 1.39, and 1.40, their index variations with temperature are -3.6×10$^{-4}$/° C., -4×10$^{-4}$/° C., and -4×10$^4$/° C., respectively. By the sensitivity curve of Bragg wavelength difference between core mode and cladding mode versus the analyte $n_t$ in FIG. 4, we have d$\lambda$/d$n_t$=2.900 nm for the refractive index of 1.40. Thus the change of Bragg wavelength difference between the core mode and cladding mode with the temperature change is about -1.1 pm/° C., which is partially compensated by a positive shift resulting from the difference of the thermo-optic and thermo-mechanical effects in the core and the cladding. The Ge-doped SiO$_2$ core has higher thermo-optic and thermo-mechanical effects than the pure SiO$_2$ cladding. From the experimental results of $n_t$=1 in FIG. 8, the positive shift in the Bragg wavelength difference is about +0.6 pm/° C. Therefore, the Bragg wavelength difference should change with temperature by about -0.5 pm/° C.

With the same method, the temperature stability of the device was investigated by considering the variation of TE and TM modes. The variation of $\Delta\lambda_{TM-TE}$ with temperature (22° C. to 65° C.) was measured by the ridge waveguide Bragg grating refractometer whose core size is 6.6 μm× 5.6 μm and the top layer is air only. The variation of $\Delta\lambda_{TM-TE}$ with temperature is less than 0.2 pm/° C. The temperature dependence of the Bragg resonance for TE mode was similar to that of the Bragg resonance for TM mode.

In Bragg grating waveguide structures, the resonant wavelengths of fundamental harmonic backward and forward propagating modes may be written as:

$$\lambda_{ResBkwd} = (n_{eff,In} + n_{eff,Bkwd})\Lambda \quad (1)$$

$$\lambda_{ResFwd} = (n_{eff,In} - n_{eff,Fwd})\Lambda \quad (2)$$

where $\Lambda$ is the grating period, $n_{eff,In}$ is the effective refractive index of the incident mode, $n_{eff,Bkwd}$ is the effective refractive index of the backward propagating coupled mode, $n_{eff,Fwd}$ is the effective refractive index of the forward propagating coupled mode. The core mode Bragg wavelength is produced when the effective refractive indices of the incident mode and the backward propagating coupled mode are equal to the core effective refractive index of the waveguide. With Eq. (1), we have $$\lambda_{core} = 2n_{eff,core}\Lambda \quad (3)$$

Cladding mode resonances are produced when the light propagating in the forward direction along the core is coupled into the cladding by the Bragg grating. From Eq. (1) for backwards scattering, we have $$\lambda_{cladding} = (n_{eff,core} + n_{eff,cladding})\Lambda \quad (4)$$

With this in mind, for scattered core and cladding modes, co-directionally propagating in either the forward or backward direction, the difference in wavelength shift as a function of the analyte index variation $\Delta n_t$ can be expressed as:

$$\Delta(\lambda_{core} - \lambda_{cladding})/\Delta n_t = [1 - (\Delta n_{eff,claddin}/\Delta n_{eff,core})](\Delta n_{eff,core}/\Delta n_t)\Lambda \quad (5)$$

We have the relative evanescent sensitivity $$S = [1 - (\Delta n_{eff,cladding}/\Delta n_{eff,core})](\Delta n_{eff,core}/\Delta n_t) \quad (6)$$

By increasing the values of $[1-(\Delta n_{eff,cladding}/\Delta n_{eff,core})]$, and $\Delta n_{eff,core}/\Delta n_t$, S can be made more sensitive to the change of the analyte $n_t$. The value of $n_{eff,core}$ can be obtained by a simple numerical method [12]. The relationship of $n_{eff,cladding}$ and $n_{eff,core}$ can be obtained from the experimental results.

To calculate the effective index $n_{eff,core}$ of the ridge waveguide structure, the numerical method developed by Mittra et al. in *IEEE Trans. Microwave Theory Technol.* MTT-288, pp. 36-43, 1980, incorporated herein by reverence, was used. According to this method, the effective index $n_0$ of the guided $n_{TM}$ core mode is given by:

$$n_{TM}^2 = \acute{n}_{TM}^2 - m^2\pi^2/4a^2k^2[1 - 2/ak(n_g^2 - n_t^2)^{1/2}] \quad (7)$$

while the effective index $n_{TE}$ of the guided TE core mode is given by:

$$n_{TE}^2 = \acute{n}_{TE}^2 - m^2\pi^2/4a^2k^2[1 - 2/ak(n_g^2 - n_t^2)^{1/2} + 2(n_g^2 - n_t^2)^{1/2}/akn_g^2] \quad (8)$$

where $k=2\pi/\lambda$ is a frequency's free-space wave number. $\acute{n}_{TE}$ and $\acute{n}_{TM}$ are the effective indices of TE and TM modes associated with the three layer slab prior to waveguide formation/etching, a is the width of the ridge waveguide, and $n_g$, $n_s$, $n_t$ are refractive indices of the core, substrate and the surrounding regions. Consider how to increase $\Delta n_{eff,\,core}/\Delta n_t$ by optimizing the waveguide structure. Equations (6) and (7) yield the following expressions for the TM and TE mode:

$$\Delta n_T/\Delta n_t = \acute{S}_{TM}(\acute{n}_{TM}/n_{TM}) + (n_t/n_{TM})(m^2\pi^2/4a^3k^3)[1/(n_g^2 - n_t^2)^{3/2}] \quad (9)$$

$$\Delta n_{TE}/\Delta n_t = \acute{S}_{TE}(\acute{n}_{TE}/n_{TE}) + (n_t/n_{TE})(m^2\pi^2/4a^3k^3)[1/(n_g^2 - n_t^2)^{3/2} + 1/n_g^2(n_g^2 - n_t^2)^{1/2}] \quad (10)$$

where $\acute{S}_{TE} = \partial\acute{n}_{TE}/\partial n_t$ and $\acute{S}_{TM} = \partial\acute{n}_{TM}/\partial n_t$. $\acute{S}_{TE}$ and $\acute{S}_{TM}$ are the sensitivities of TE and TM modes for the three layer slab prior to waveguide formation/etching. As $\acute{n}_{TE} \approx n_{TE}$ and $\acute{n}_{TM} \approx n_{TM}$, the first terms in equations (9) and (10) are dominated by $\acute{S}_{TE}$ and $\acute{S}_{TM}$. By the normalized analysis of a slab waveguide evanescent-wave sensor, the expressions of $\acute{S}_{TE}$ and $\acute{S}_{TM}$ are given in Dai et al. *Meas. Sci. Technol.* 17, pp. 1752-1756, 2006, incorporated herein by reference and optimization results for all slab waveguide sensors are achieved. However, these results cannot be applied directly to ridge waveguides due to the structural difference of the three layer slab waveguides and the ridge waveguides. The structural characteristic of ridge waveguides have a much more significant impact on the second terms of equations (9) and (10) as is reflected by the presence of parameters a, $n_g$ and $n_t$.

Secondly, let us consider how to obtain the detailed information on the effective index $n_{eff,\,cladding}$. With the experimental results, we note that a relationship exists between the ratio of the cladding/core wavelength shifts and the waveguide width α. This data has been fitted to the quadratic expression provided in equation (11).

$$\Delta\lambda_{clad}/\Delta\lambda_{core} = 0.019193\alpha^2 - 0.169547\alpha + 1.000000 \quad (11)$$

where, 5.7 μm ≤ α ≤ 7.7 μm. With Eqs. (3) and (4), we have the expression for $\Delta n_{eff,cladding}/\Delta n_{eff,core}$:

$$\Delta n_{eff,cladding}/\Delta n_{eff,core} = 2\Delta\lambda_{clad}/\Delta\lambda_{core} - 1 = 0.038386\alpha^2 - 0.339094\alpha + 1 \quad (12)$$

Substituting Eqs. (9), (10), and (12) into Eq. (6) yields the expression of the relative evanescent sensitivity S.

$$S_{TM} = (0.339094a - 0.038386a^2)\left\{\begin{array}{l}\acute{S}_{TM} + (n_t/n_{TM}) \\ (m^2\pi^2/4a^3k^3)[1/(n_g^2 - n_t^2)^{3/2}]\end{array}\right\} \quad (13)$$

$$= \acute{S}_{TM}(0.339094a - 0.038386a^2) +$$

-continued
$$(0.339094a - 0.03836a^2)[(n_t/n_{TM})(m^2\pi^2/4a^3k^3)[1/(n_g^2 - n_t^2)^{3/2}]$$

$$S_{TE} = (0.339094a - 0.038386a^2)\left\{\begin{array}{l}\acute{S}_{TE} + (n_t/n_{TE})(m^2\pi^2/4a^3k^3) \\ [1/(n_g^2 - n_t^2)^{3/2} + 1/n_g^2(n_g^2 - n_t^2)^{1/2}]\end{array}\right\} \quad (14)$$

$$= \acute{S}_{TE}(0.339094a - 0.038386a^2) +$$

$$\left(\begin{array}{l}0.339094a - \\ 0.038386a^2\end{array}\right)\left[(n_t/n_{TE})(m^2\pi^2/4a^3k^3)\right]\left[\begin{array}{l}1/(n_g^2 - n_t^2)^{3/2} + \\ 1/n_g^2(n_g^2 - n_t^2)^{1/2}\end{array}\right]$$

Figure 9:
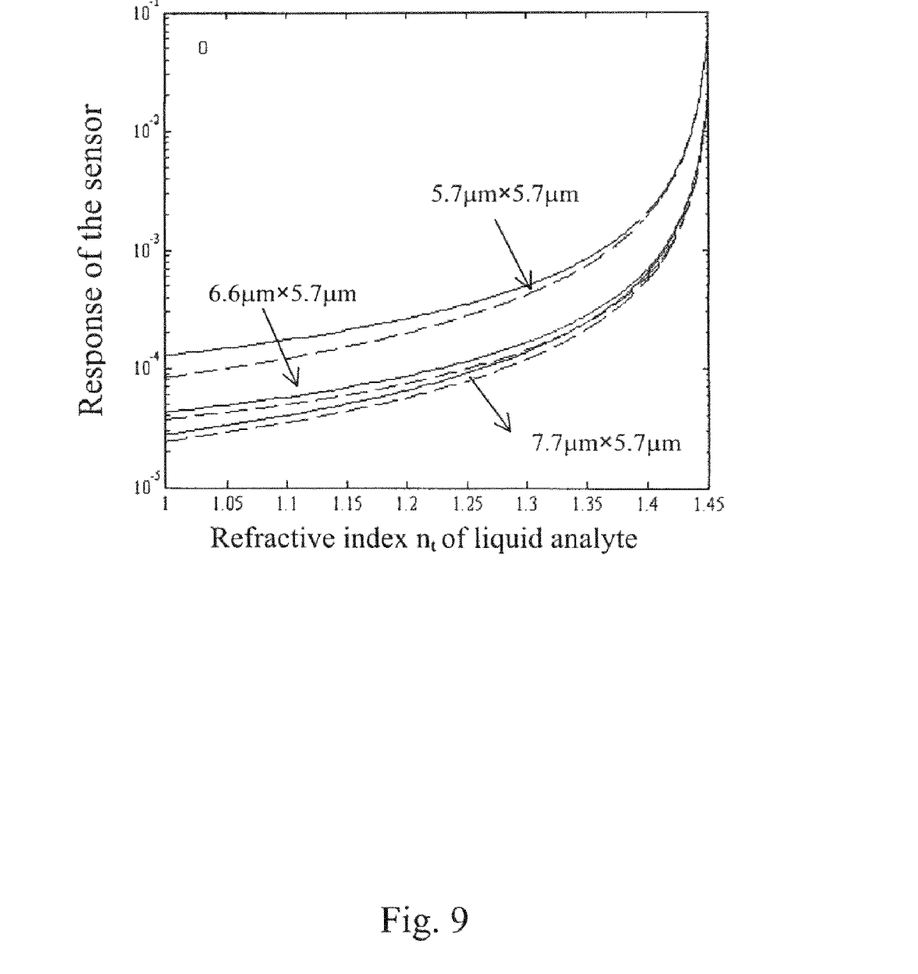
FIG. 9 presents the response of the sensor changing with waveguide core size and external index in the range of 1~1.4545 (solid line for TM mode, dash line for TE mode) by considering the variation of core and cladding modes.

$\acute{S}_{TE}$ and $\acute{S}_{TM}$ are the sensitivities for the three layer slab prior to waveguide formation/etching as defined by Parriaux et al. in *J. Lightwave Technol.* 16, pp. 573-582, 1998, incorporated herein by reference. Their change is related to the thickness variation of the core layer and not to the width variation of the ridge waveguide. To explain how the width variation of the ridge waveguides impacts on the sensitivity, the second terms in equations (13) and (14) are considered. The results are plotted in FIG. 9 with the analyte index n, changing from 1 to 1.454 for waveguides with core size are 5.7 μm×5.7 μm, 6.6 μm×5.7 μm, and 7.7 μm×5.7 μm, respectively. FIG. 9 shows that the sensor response increases slowly in the low refractive index region, but increases rapidly as the index of the surrounding medium approaches that of the waveguide. For the range of waveguide widths investigated, the sensitivity also increases as the core width decreases. More specifically we observe that as the analyte index n, approaches the core index $n_g$=1.4545, the relative evanescent sensitivity is maximized. The simulation results in FIG. 4 show the core and cladding mode effective indexes, and their difference shift with the change of the refractive index of the analyte liquid, respectively, they are agreement with the experimental results.

The waveguide birefringence results in a Bragg grating wavelength polarization-dependence that is $$\lambda_{TM} - \lambda_{TE} = 2\Lambda(n_{TM} - n_{TE}) \quad (15)$$

where $\lambda_{TM}$, $\lambda_{TE}$ are the Bragg wavelengths for TM and TE modes, respectively. In the experiments, the TE and TM resonances are varied with the external refractive index $n_t$. The difference in the wavelength shifts as a function of the analyte index variation $\Delta n_t$ can be expressed as:

$$\Delta(\lambda_{TE} - \lambda_{TM})/\Delta n_t = 2(\Delta n_{eff,TE} - \Delta n_{eff,TM})/(\Delta n_t)/\Lambda \quad (16)$$

Here, $(\Delta n_{eff,TE} - \Delta n_{eff,TM})/(\Delta n_t)$ is the relative evanescent sensitivity.

The equations (7) and (8) yield the following expressions for TM and TE modes:

$$\Delta n_{TM}/\Delta n_t = \acute{S}_{TM}(\acute{n}_{TM}/n_{TM}) + (n_t/n_{TM})(m^2\pi^2/4a^3k^3)[1/(n_g^2 - n_t^2)^{3/2}] \quad (17)$$

$$\Delta n_{TE}/\Delta n_t = \acute{S}_{TE}(\acute{n}_{TE}/n_{TE}) + (n_t/n_{TE})(m^2\pi^2/4a^3k^3)[1/(n_g^2 - n_t^2)^{3/2} + 1/n_g^2(n_g^2 - n_t^2)^{1/2}] \quad (18)$$

where $\acute{S}_{TE} = \partial\acute{n}_{TE}/\partial n_t$ and $\acute{S}_{TM} = \partial\acute{n}_{TM}/\partial n_t$. $\acute{S}_{TE}$ and $\acute{S}_{TM}$ are the sensitivities of TE and TM modes for the three layer slab prior to waveguide formation/etching. As $\acute{n}_{TE} \approx n_{TE}$ and $\acute{n}_{TM} \approx n_{TM}$, the first terms in equations (6) and (7) are dominated by $\acute{S}_{TE}$ and $\acute{S}_{TM}$. With Eqs. (6) and (7), we have the equation for relative evanescent sensitivity $$S = (\acute{S}_{TM} - \acute{S}_{TE}) + (m^2\pi^2/4a^3k^3)\{(n_t/n_{TM})1/(n_g^2 - n_t^2)^{3/2} - (n_t/n_{TE})[1/(n_g^2 - n_t^2)^{3/2} + 1/n_g^2(n_g^2 - n_t^2)^{1/2}]\} \quad (19)$$

Figure 10:
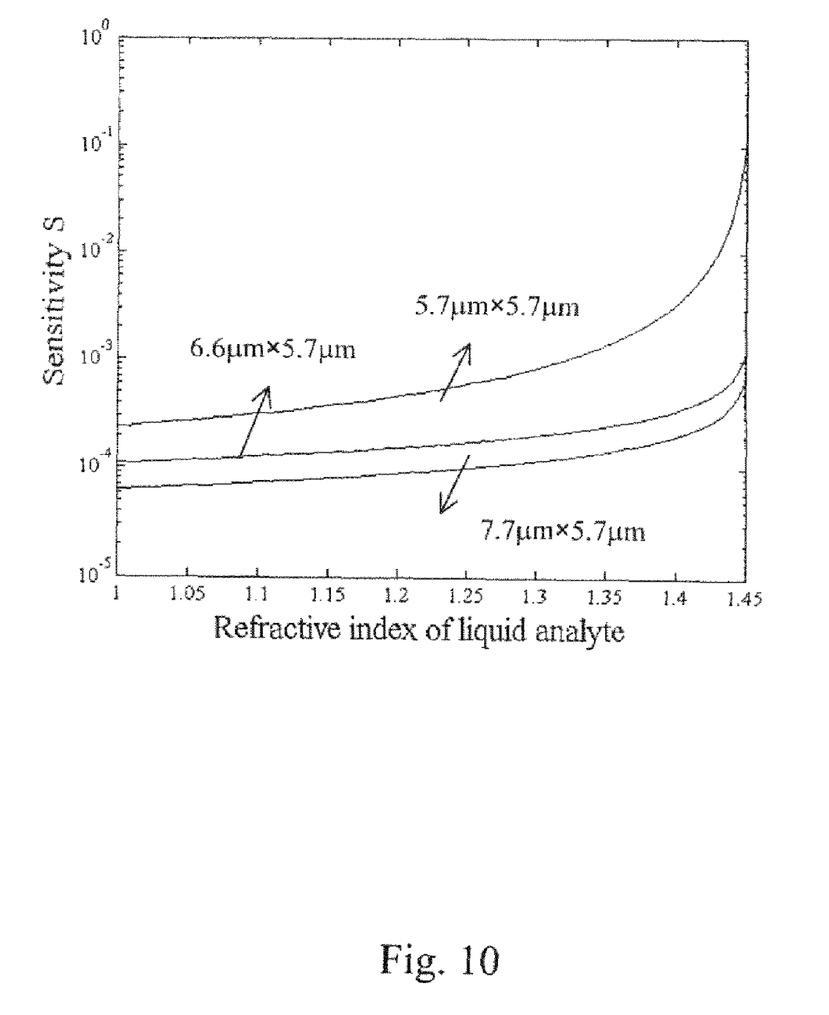
FIG. 10 presents the response of the sensor changing with waveguide core size and external index in the range of 1~1.4545 by considering the variation of TE and TM modes.

The structural characteristic of ridge waveguides have a much more significant impact on the second term of Eq. (8) as is demonstrated by the presence of parameters a, $n_g$ and $n_t$. $\acute{S}_{TE}$ and $\acute{S}_{TM}$ are the sensitivities for the three layer slab prior to waveguide formation/etching. Their change is related to the thickness variation of the core layer and not to the width variation of the ridge waveguide. To explain how the width variation of the ridge waveguides impacts on the sensitivity, the second terms in equations (19) is considered. The results are plotted in FIG. 9 with the analyte index n, changing from 1 to 1.454 for waveguides with core size are 5.7 μm×5.7 μm, 6.6 μm×5.7 μm, and 7.7 μm×5.7 μm, respectively. FIG. 10 shows that the sensor response increases slowly in the low refractive index region, but increases rapidly as the index of the surrounding medium approaches that of the waveguide. For the range of waveguide widths investigated, the sensitivity also increases as the core width decreases. More specifically we observe that as the analyte index n, approaches the core index $n_g$=1.4545, the relative evanescent sensitivity is maximized. The simulation results in FIG. 9 show the difference of TE and TM modes shifts with the change of the refractive index of the analyte liquid, which are in agreement with the experimental results.

To overcome the temperature instability in a high sensitivity open-top ridge waveguide refractometer that incorporates a Bragg grating, a highly temperature insensitive refractometer is developed that uses one grating mode resonance as a temperature reference and the relative shift of another grating mode resonance to measure the refractive index change of a top layer of liquid. As the two Bragg modes propagate in different locations within the open-top ridge waveguide structure, the two resonances have similar sensitivities to the temperature but different sensitivities to the external refractive index above the top layer. The shifting of the difference of the core and cladding resonances for variations in the external refractive index from 1.418 to 1.4544 is 1 pm of wavelength shift for 5×10$^{-5}$ change of the external refractive index at a probe wavelength of 1550 nm. The shifting of the difference of the core and cladding resonances to the temperature change is about 0.5 pm/° C. The shifting of the difference of TE and TM resonances for variations in the external refractive index from 1.425 to 1.4544 is 1 pm of wavelength shift for 3×10$^{-4}$. Ultraviolet laser induced birefringence of the ridge waveguide can also be oriented in order to enhance the inherent waveguide birefringence of the waveguide which would improve the sensitivity of the refractometer when considering polarization dependent resonances. The shifting of the difference of TE and TM resonances to the temperature change is about 0.2 pm/° C. Using one mode resonance as a temperature reference, the relative shift of another mode resonance is used to measure the refractive index change of the liquid on the top only. With the developed simulation model, the higher sensitivity substantially temperature insensitive refractometer is available by optimizing the waveguide structures.

Recently Mihailov et al. in U.S. Pat. No. 6,993,221 taught a technique for inscription of a Bragg grating structure in an optical waveguide using ultrafast infrared laser pulses and a phase mask. This technique is highly advantageous, as grating inscription no longer requires the waveguide to be photosensitive to ultraviolet radiation. As a result Bragg gratings have been successfully inscribed in several optical waveguides consisting of different glasses and crystalline materials, such as fluoride based glasses, phosphate based glasses, sapphire and lithium niobate. Many of these materials have much higher indices of refraction compared to silica. In terms of the present invention, fabrication of ridge waveguides with Bragg gratings therein in substrates of Lithium niobate, sapphire, fluoride or phosphate glasses is advantageous and would permit a refractometer to measure refractive indices of analytes up to that of the waveguide material. The refractive indicies of lithium niobate and sapphire are 2.14 and 1.75 at probe wavelengths of 1550 nm respectively. Fluoride and phosphate mid infrared transmissive glasses have refractive indices of 1.49 and 1.53 respectively at a 1550 nm probe beam wavelength. If a Bragg grating is produced in a ridge waveguide made in for example sapphire, then analyte refractive indices up to the refractive index of sapphire (n=1.747) can be measured and also the analyte indices can be measured at high temperature (up to 1500 C). Using femtosecond irradiation, a Bragg grating can be localized on one side of the ridge waveguide producing, producing a Bragg grating with a highly birefringent spectral response. Similarly III-V materials could be used to fabricate ridge waveguides in materials such as gallium arsenide and silicon that have high refractive indices (see for example Leonburger et al. U.S. Pat. No. 4,518,219). Silicon based optical waveguides are possible in the telecommunication band of 1550 nm. Using longer wavelength femtosecond infrared radiation (for example 1550 nm), that is longer than the absorption band wavelength of silicon, Bragg gratings could be inscribed in a silicon based waveguide. Silicon has a refractive index in the telecommunication band of ~3.5. It is advantageous to consider ridge waveguide refractometers made in single crystal semiconductor layers as techniques for their fabrication have been well established for the microelectronics industry.

What is claimed is:

1. An optical sensor for sensing information relating to an analyte liquid or gas, comprising:
   a planar substrate having a refractive index $n_c$;
   a ridge waveguide having at least a region thereof unclad and having a refractive index $n_r$, wherein said ridge waveguide is formed upon and supported by substrate, and wherein the substrate serves as cladding layer for the ridge waveguide at a location where the ridge waveguide contacts the substrate; and,
   a Bragg grating having at least two resonance modes for providing information relating to both temperature and refractive index of the surrounding analyte liquid or gas, wherein a first resonance mode has a different response to the analyte when compared to a second resonance mode, while both modes have a same reaction to temperature, wherein said Bragg grating is formed within the unclad region of ridge waveguide, wherein $n_c < n_r$.

2. An optical sensor as defined in claim 1 wherein the first resonance mode is a cladding mode and the second resonance mode is a Bragg resonance mode.

3. An optical sensor as defined in claim 1 wherein the first resonance mode is the TE polarization mode of the Bragg resonance and the second resonance mode is the TM polarization mode of the Bragg resonance.

4. An optical sensor as defined in claim 1 wherein the sensor includes only a single Bragg grating, and wherein the Bragg grating has a polarization dependent response.

5. An optical sensor as defined in claim 1, wherein the sensor includes only a single Bragg grating and wherein the Bragg grating is written with a beam having its polarization in a direction along the waveguide so as to enhance a difference in the TE and TM modes of the Bragg grating.

6. An optical sensor as defined in claim 5 wherein the TE and TM modes of the Bragg grating are substantially different such that one of the TE and TM modes is significantly greater than a natural birefringence in a length of said waveguide wherein the Bragg grating is absent.

7. An optical sensor as defined in claim 4, wherein the ridge waveguide has a square or rectangular cross-section and wherein at least three sides of the ridge waveguide are unclad in the unclad region and wherein the substrate provides a structural cladding to the unclad ridge waveguide and wherein the surrounding environment provides a functional cladding to the unclad ridge waveguide.

8. A sensor as defined in claim 1 further comprising means for containing an analyte about the Bragg grating so as to lessen running off of the analyte to be tested.

9. A sensor as defined in claim 1 further comprising two ridges formed within or upon the substrate essentially parallel to the ridge waveguide, for containing analyte about the ridge waveguide.

10. A sensor as defined in claim 1, wherein the core has a width that is less than half of the height of the core.

11. A sensor as defined in claim 1 wherein the refractive index of the core is $\leq 1.44$.

12. A sensor as defined in claim 1 wherein the refractive index difference between the core and the substrate is approximately 0.001.

13. A sensor as defined in claim 1 wherein Bragg grating is inscribed by femto-second irradiation of light.

14. A sensor as defined in claim 1 wherein the entire supported ridge waveguide is unclad on three sides.

15. A sensor as defined in claim 4 further comprising:
a single mode input optical fiber optically coupled to an input end face of the ridge waveguide and, a single mode output optical fiber optically coupled to an opposing output end face of the ridge waveguide for transporting light into the ridge waveguide and for transporting light out of the ridge waveguide, respectively.

16. An optical sensor as defined in claim 12, wherein the sensor includes a broadband light source and an analyzer for analyzing light output on the single mode output optical fiber.

17. An optical sensor as defined in claim 15 wherein the broadband light source has a range of wavelengths between 1480 to 1580 nm.

18. An optical sensor as defined in claim 1, wherein the sensor is a refractometer and wherein ridge waveguide is mounted on a block in which liquid is circulated.

19. The use of the sensor as defined in claim 1, wherein one grating resonance mode is used as a temperature reference and wherein a relative shift of another grating resonance mode is used to measure the refractive index change of the analyte liquid or gas contacting the unclad ridge waveguide about the Bragg grating.

20. The use of the sensor in claim 1 wherein polarization and cladding resonance modes are used to measure up to three parameters.

21. The use of the sensor as defined in claim 20 wherein the parameters include one of temperature, strain, bending and refractive index.

22. The use of the sensor as defined in claim 20 wherein the parameters include pressure of the fluid.

23. The sensor as defined in claim 1, wherein the Bragg grating is a tilted grating so as to enhance coupling into cladding modes or produce radiation modes.

* * * * *